United States Patent [19]

Hausberg et al.

[11] 4,251,538
[45] Feb. 17, 1981

[54] INDOLEALKYLAMINES AND PROCESSES FOR THEIR PREPARATION

[75] Inventors: Hans-Heinrich Hausberg; Volker Koppe; Eike Poetsch; Otto Saiko; Christoph Seyfried, all of Darmstadt, Fed. Rep. of Germany

[73] Assignee: Merck Patent Gesellschaft mit beschrankter Haftung, Darmstadt, Fed. Rep. of Germany

[21] Appl. No.: 51,320

[22] Filed: Jun. 22, 1979

[30] Foreign Application Priority Data

Jun. 24, 1978 [DE] Fed. Rep. of Germany ....... 2827874
Mar. 16, 1979 [DE] Fed. Rep. of Germany ....... 2910367

[51] Int. Cl.³ .................. A61K 31/445; C07D 209/08
[52] U.S. Cl. .................................... 424/267; 546/273; 546/201
[58] Field of Search .................. 546/273, 201; 424/267

[56] References Cited

U.S. PATENT DOCUMENTS

| 3,217,011 | 11/1965 | Zenitz | 546/273 |
| 3,238,215 | 3/1966 | Zenitz | 546/273 |
| 3,494,920 | 2/1970 | Herbst | 546/273 |
| 3,639,414 | 2/1972 | Archer | 546/273 |
| 3,821,234 | 6/1974 | Koppe et al. | 546/273 |
| 4,021,431 | 5/1977 | Zenitz | 546/273 |

FOREIGN PATENT DOCUMENTS 921507 4/1961 United Kingdom ..................... 546/273

Primary Examiner—Henry R. Jiles
Assistant Examiner—Robert C. Whittenbaugh
Attorney, Agent, or Firm—Millen & White

[57] ABSTRACT

Indolealkylamines of the formula

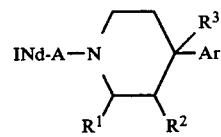

wherein Ind is 1-$R^4$-2-$R^5$-indol-3-yl or the corresponding group in which the benzene ring is monosubstituted to trisubstituted by alkyl, O-alkyl, S-alkyl, OH, F, Cl, Br, $CF_3$ or CN; A is —$(CH_2)_4$—, —$(CH_2)_3$—CO— or —CO—$(CH_2)_2$—CO—; $R^1$ is H or methyl; $R^2$ is H or together with $R^3$ is a C—C bond; $R^3$ is H or together with $R^2$ is a C—C bond; $R^4$ and $R^5$ are each H, alkyl, or phenyl; and Ar is phenyl or phenyl monosubstituted or disubstituted by alkyl, F, Cl, Br, I or $CF_3$; wherein alkyl in each case is of 1-4 carbon atoms;

and the physiologically acceptable acid addition salts thereof possess valuable pharmacological properties.

12 Claims, No Drawings

INDOLEALKYLAMINES AND PROCESSES FOR THEIR PREPARATION

The present invention relates to new indolealkylamines.

SUMMARY OF THE INVENTION

It is an object of the present invention to provide new indolealkylamines having pharmacological properties.

Upon further study of the specification and appended claims, further objects and advantages of this invention will become apparent to those skilled in the art.

These objects have been attained by providing new indolealkylamines of formula I

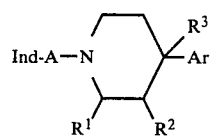

wherein Ind is $1\text{-}R^4\text{-}2\text{-}R^5\text{-indol-3-yl}$ in which the benzene ring can be monosubstituted to trisubstituted by alkyl, O-alkyl, S-alkyl, OH, F, Cl, Br, $CF_3$ and/or CN; A is $-(CH_2)_4-$, $-(CH_2)_3-CO-$ or $-CO-(CH_2)_2-CO$; $R^1$ is H or methyl; $R^2$ is H or together with $R^3$ is a C—C bond; $R^3$ is H or together with $R^2$ is a C—C bond; $R^4$ and $R^5$ are each H, alkyl or phenyl; and Ar is phenyl which is unsubstituted or monosubstituted or disubstituted by alkyl, F, Cl, Br, I and/or $CF_3$; and wherein the alkyl groups in each case possess 1–4 carbon atoms, and their physiologically acceptable acid addition salts.

DETAILED DISCUSSION

In the radicals Ind, $R^4$, $R^5$ and Ar, alkyl is preferably methyl and also ethyl, n-propyl, isopropyl, n-butyl, isobutyl, sec-butyl or tert-butyl. O-Alkyl is preferably methoxy and also ethoxy, n-propoxy, isopropoxy, n-butoxy, isobutoxy, sec-butoxy or tert-butoxy. S-Alkyl is preferably methylthio, but also ethylthio, n-propylthio, isopropylthio, n-butylthio, isobutylthio, sec-butylthio or tert-butylthio.

The radical Ind is in particular an unsubstituted indol-3-yl radical. If, however, Ind is a substituted indol-3-yl radical it is preferably monosubstituted, especially in the 1-, 2- or 5-position. Substitution in the 4-, 6- or 7-position is also possible. Preferred disubstituted indol-3-yl radicals are substituted in the 1,2-, 1,5-, 2,5-, 4,7-, 5,6- or 5,7-positions; disubstitution is also possible in the 1,4-, 1,6-, 1,7-, 2,4-, 2,6-, 2,7-, 4,5-, 4,6- or 6,7-positions. In all of these cases the substituents can be identical or different. Preferred trisubstituted indol-3-yl radicals are substituted in the 1,2,5-, 4,5,6- or 5,6,7-positions; trisubstitution is also possible in the 1,2,4-, 1,2,6-, 1,2,7-, 1,4,5-, 1,4,6-, 1,4,7-, 1,5,6-, 1,5,7-, 1,6,7-, 2,4,5-, 2,4,6-, 2,4,7-, 2,5,6-, 2,5,7-, 2,6,7-, 4,5,7- or 4,6,7-positions.

Tetrasubstitution of the indole ring is also possible in the 1,2,4,5-, 1,2,4,6-, 1,2,4,7-, 1,2,5,6-, 1,2,5,7-, 1,2,6,7-, 1,4,5,6-, 1,4,5,7-, 1,4,6,7-, 1,5,6,7-, 2,4,5,6-, 2,4,5,7-, 2,4,6,7- or 2,5,6,7-positions and pentasubstitution is possible in the 1,2,4,5,6-, 1,2,4,5,7-, 1,2,4,6,7-, or 1,2,5,6,7-positions.

In detail, the preferred substituents in the benzene ring of the radical Ind are methyl, ethyl, methoxy, ethoxy, methylthio, ethylthio, OH, F, Cl, Br, $CF_3$ and CN. $R^4$ is preferably H or methyl and $R^5$ is preferably H, methyl or phenyl. Accordingly, some preferred meanings of the radical Ind are indol-3-yl and also 1-, 2-, 4-, 5-, 6- or 7-methylindol-3-yl, 1-, 2-, 3-, 4-, 5-, 6- or 7-ethyl-indol-3-yl, 1- or 2-phenylindol-3-yl, 4-, 5-, 6- or 7-methoxyindol-3-yl, 4-, 5-, 6- or 7-ethoxyindol-3-yl, 4-, 5-, 6- or 7-methylthioindol-3-yl, 4-, 5-, 6- or 7-ethylthioindol-3-yl, 4-, 5-, 6- or 7-fluoroindol-3-yl, 4-, 5-, 6- or 7-chloroindol-3-yl, 4-, 5-, 6- or 7-bromoindol-3-yl, 4-, 5-, 6- or 7-trifluoromethyl-indol-3-yl, 4-, 5-, 6- or 7-cyanoindol-3-yl, 1,2-, 1,4-, 1,5-, 1,6-, 1,7-, 2,4-, 2,5-, 2,6-, 2,7-, 4,5-, 4,6-, 4,7-, 5,6-, 5,7- or 6,7-dimethylindol-3-yl, 1-methyl-2-phenylindol-3-yl, 2-phenyl-4-, -5-, -6- or -7-methylindol-3-yl, 1-methyl-4-, -5-, -6- or -7-methoxyindol-3-yl, 1-methyl-4-, -5-, -6- or -7-methylthioindol-3-yl, 1-methyl-4-, -5-, -6- or -7-fluoroindol-3-yl, 1-methyl-4-, -5-, -6- or -7-chloroindol-3-yl, 1-methyl-4-, -5-, -6- or -7-bromoindol-3-yl, 1-methyl-4-, -5-, -6- or -7-trifluoromethylindol-3-yl, 1-methyl-4-, -5-, -6- or -7-cyanoindol-3-yl, 2-methyl-4-, -5-, -6- or -7-methoxyindol-3-yl, 2-methyl-4-, -5-, -6- or -7-methylthioindol-3-yl, 2-methyl-4-, -5-, -6- or -7-fluoroindol-3-yl, 2-methyl-4-, -5-, -6- or -7-chloroindol-3-yl, 2-methyl-4-, -5-, -6- or -7-bromoindol-3-yl, 2-methyl-4-, -5-, -6- or -7-trifluoromethylindol-3-yl, 2-methyl-4-, -5-, -6- or -7-cyanoindol-3-yl, 4-methyl-5-fluoroindol-3-yl, 5-fluoro-6- or -7-methylindol-3-yl, 4-methyl-5-chloroindol-3-yl, 4-chloro-5-methylindol-3-yl, 5-methyl-6- or -7-chloroindol-3-yl, 5-chloro-6- or -7-methylindol-3-yl, 4,5-, 4,6-, 4,7-, 5,6-, 5,7- or 6,7-dimethoxyindol-3-yl, 4,5-, 4,6-, 4,7-, 5,6-, 5,7- or 6,7-dichloroindol-3-yl, 4-trifluoromethyl-5-, -6- or -7-chloroindol-3-yl, 1,2,4-, 1,2,5-, 1,2,6-, 1,2,7-, 1,4,5-, 1,4,6-, 1,4,7-, 1,5,6-, 1,5,7-, 1,6,7-, 2,4,5-, 2,4,6-, 2,4,7-, 2,5,6-, 2,5,7- or 2,6,7-trimethylindol-3-yl, 4,5,6-, 4,5,7-, 4,6,7- or 5,6,7-trimethoxyindol-3-yl and 4,5,6-, 4,5,7-, 4,6,7- or 5,6,7-trichloroindol-3-yl.

The group A is preferably $-(CH_2)_4-$.

$R^1$ is preferably H. $R^2$ and $R^3$ are preferably together a C—C bond.

The radical Ar is preferably unsubstituted phenyl. If Ar is a substituted phenyl group, this is preferably monosubstituted. It can, however, also be disubstituted, in which case the substituents can be identical or different. Preferred substituents on the phenyl group are methyl, F, Cl, Br and trifluoromethyl. In detail, Ar is preferably phenyl, o-, m- or p-fluorophenyl, o-, m- or p-chlorophenyl, o-, m- or p-bromophenyl, o-, m- or p-tolyl, o-, m- or p-trifluoromethylphenyl and also, for example, o-, m- or p-ethylphenyl, o-, m- or p-n-propylphenyl, o-, m- or p-isopropylphenyl, o-, m- or p-n-butylphenyl, o-, m- or p-isobutylphenyl, o-, m- or p-iodophenyl and also dihalogenophenyl, e.g., 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-fluoro-4-chlorophenyl or 2-bromo-4-chlorophenyl; dimethylphenyl, e.g., 2,3-, 2,4-, 2,5-, 2,6-, 3,4- or 3,5-dimethylphenyl; or methyl-chlorophenyl, e.g., 2-methyl-4-chlorophenyl.

Accordingly, the invention relates in particular to those compounds of the formula I in which at least one of the radicals mentioned has one of the meanings indicated above, especially one of the preferred meanings indicated above. Some preferred groups of compounds can be expressed by the following partial formulae Ia to Ih, which correspond to the formula I and in which the radicals not designated in detail have the meaning indicated under formula I, but in which in Ia, Ind is indol-3-yl, 1-methyl-indol-3-yl or 2-methyl-indol-3-yl;
in Ib, A is —(CH$_2$)$_4$—;
in Ic, R$^1$ is H;
in Ie, R$^2$ and R$^3$ together are a C—C bond;
in If, Ar is phenyl, p-fluorophenyl, o- or p-chlorophenyl, o- or p-bromophenyl, p-tolyl or m-trifluoromethylphenyl;
in Ig, Ind is indol-3-yl, 1-methylindol-3-yl or 2-methylindol-3-yl, A is —(CH$_2$)$_4$— and Ar is phenyl, p-chlorophenyl or m-trifluoromethylphenyl; and
in Ih, Ind is indol-3-yl, 1-methylindol-3-yl or 2-methylindol-3-yl, A is —(CH$_2$)$_4$—and Ar is phenyl.

The compounds of the formula I can possess one or more asymmetric carbon atoms. They can therefore be in the form of racemates and if several asymmetric carbon atoms are present also in the form of mixtures of several racemates as well as in diverse optically active forms.

The invention also relates to a process for the preparation of the compounds of formula I and their physiologically acceptable acid addition salts, comprising (a) reacting a compound of formula II

Ind-A-X$^1$                       (II)

wherein X$^1$ is X or NH$_2$ and X is Cl, Br, I, OH or a reactively functionally modified OH group and Ind and A are as defined above, with a compound of formula III

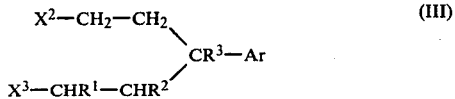

wherein X$^2$ and X$^3$ can be identical or different and, if X$^1$ is NH$_2$, are in each case X and otherwise together are NH, and R$^1$, R$^2$, R$^3$ and Ar are as defined above;

(b) cyclizing an isonitrile of formula IV

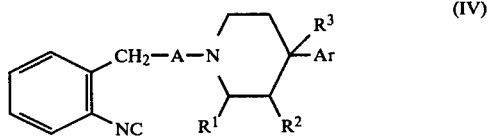

which in the benzene ring can be monosubstituted to trisubstituted by alkyl, O-alkyl, S-alkyl, OH, F, Cl, Br, CF$_3$ and/or CN and wherein R$^1$, R$^2$, R$^3$, A and Ar are as defined above, in the presence of lithium 2,2,6,6-tetramethylpiperidide;

(c) reducing a pyridinium salt of formula V

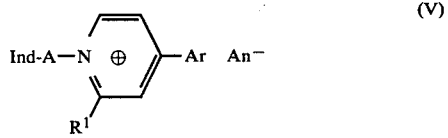

wherein An$^-$ is an anion of a strong acid and Ind, A, R$^1$ and Ar are as defined above with a reducing agent; and/or (d) optionally, in a compound of formula I, reducing one or two CO groups to CH$_2$ groups, and/or hydrogenating a double bond, and/or alkylating a free NH group in the indole ring, and/or splitting an alkoxy group with formation of a hydroxy group, and/or converting a base of the formula I by treatment with an acid to one of its physiologically acceptable acid addition salts.

In other respects the preparation of the compounds of formula I is carried out in accordance with methods which are in themselves known, e.g., as are described in the literature (for example in the standard works, e.g., Houben-Weyl, Methoden der Organischen Chemie (Methods of Organic Chemistry), Georg-Thieme-Verlag, Stuttgart; and Organic Reactions, John Wiley & Sons, Inc., New York), and in particular under reaction conditions which are known and suitable for the mentioned reactions. It is also possible to make use of variants which are in themselves known and are not mentioned in more detail here.

The starting materials of the formulae II to V can, if desired, also be formed in situ, in that they are not isolated from the reaction mixture but are immediately reacted further to produce the compounds of formula I.

The compounds of formula I are preferably obtained by reacting indole derivatives of formula II with compounds of formula III.

In the indole derivatives of formula II, X$^1$ is preferably X; accordingly, in the compounds of formula III, X$^2$ and X$^3$ are preferably together NH. The radical X is preferably Cl or Br; however, it can also be I, OH or a reactively functionally modified OH group, especially alkylsulphonyloxy with 1–6 carbon atoms (for example, methanesulphonyloxy) or arylsulphonyloxy with 6–10 carbon atoms (for example benzenesulphonyloxy, p-toluenesulphonyloxy or 1- or 2-naphthalene-sulphonyloxy).

Accordingly, the indolealkylamines of formula I are in particular obtainable by reacting compounds of the formulae Ind-A-Cl or Ind-A-Br with piperidine derivatives of formula III in which X$^2$ and X$^3$ together are an NH group (designated IIIa below).

Some of the compounds of formulae II and III are known; the compounds of formulae II and III which are not known can easily be prepared analogously to the known compounds. Thus, in particular, 4-(indol-3-yl)-butyric acid and 4-(indol-3-yl)-4-oxo-butyric acid are known. The other carboxylic acids of the formulae Ind—(CH$_2$)$_3$—COOH and Ind—CO—CH$_2$CH$_2$—COOH are obtainable analogously from the corresponding indoles. Primary alcohols of formula II in which the group A-X$^1$ is a —(CH$_2$)$_4$—OH group or a —CO(CH$_2$)$_3$—OH group, for example, 4-(indol-3-yl-butanol), are obtainable, for example, by reduction of the corresponding carboxylic acids or their esters. Treatment with thionyl chloride, hydrogen bromide, phosphorus tribromide or similar halogen compounds gives the corresponding halides of formula II in which A-X$^1$=—(CH$_2$)$_4$—Cl or —(CH$_2$)$_4$—Br, for example 3-(4-chlorobutyl)-indole or 3-(4-bromobutyl)-indole. The iodine compounds, for example, 3-(4-iodobutyl)-indole, are obtained, for example, by the action of potassium iodide on the corresponding p-toluenesulphonic acid esters. The corresponding sulphonyloxy compounds are obtainable from the alcohols Ind-A-Oh by reaction with the corresponding sulphonic acid chlorides. The amines Ind-A-NH$_2$ are obtainable, for example, from the halides with phthalimide potassium or by reduction of the corresponding nitriles.

Most of the piperidine derivatives IIIa are known (compare German Offenlegungsschrift No. 2,060,816) and are obtainable, for example, by reacting 4-piperidone with metal-organic compounds of the formula Li-Ar, subsequently hydrolyzing the reaction product to the corresponding 4-Ar-4-hydroxy-piperidines and, if desired, subsequently dehydrating the latter to 4-Ar-3,4-dehydro-piperidines and hydrogenating these to 4-Ar-piperidines. Compounds of the formula III ($X^2$ and $X^3=X$ in each case) can be prepared, for example, by reducing 3-Ar-glutaric acid esters to 3-Ar-1,5-pentanediols and optionally subsequently reacting the latter with $SOCl_2$ or $PBr_3$.

The reaction of the compounds II and III proceeds according to methods which are known from the literature for the alkylation of amines. It is possible to melt the components together without a solvent being present, if appropriate in a closed tube or in an autoclave. However, it is also possible to react the compounds in the presence of an inert solvent. Suitable solvents are, for example, hydrocarbons, e.g., benzene, toluene or xylene; ketones, e.g., acetone or butanone; alcohols, e.g., methanol, ethanol, isopropanol or n-butanol; ethers, e.g., tetrahydrofuran (THF) or dioxane; amides, e.g., dimethylformamide (DMF) or N-methyl-pyrrolidone; and nitriles, e.g., acetonitrile, and optionally also mixtures of these solvents with one another or mixtures with water. The addition of an acid-binding agent, for example of an alkali metal hydroxide, carbonate or bicarbonate or alkaline earth metal hydroxide, carbonate or bicarbonate or of another alkali metal or alkaline earth metal saklt of a weak acid, preferably the potassium, sodium or calcium salt, or the addition of an organic base, e.g., triethylamine, dimethylaniline, pyridine or quinoline, or of an excess of the amine component Ind-A-$NH_2$ or of the piperidine derivative of the formula IIIa can be advantageous. Acid piperidides of the formula I (A=—$(CH_2)_3$—CO—) can be prepared, for example, from the free carboxylic acids of formula II (A-$X^1$=—$(CH_2)_3$—COOH) and piperidine derivatives of formula IIIa in the presence of a dehydrating agent, for example, carbonyldiimidazole or dicyclohexylcarbodiimide, in one of the inert solvents indicated, preferably THF.

Depending on the conditions employed, the reaction time is from a few minutes to 14 days and the reaction temperature is from about 0° to 150° C. and usually from 20° to 130° C.

According to a variant of the above method, it is possible to react a compound which corresponds to formula II but possesses a carbonyl group in place of a —CHX group, especially an aldehyde of the formula Ind—$(CH_2)_3$—CHO or Ind—CO—$(CH_2)_2$—CHO, with an amine of formula IIIa under the conditions of a catalytic hydrogenation. The reaction conditions correspond to those known from the literature for reductive alkylations; the corresponding aldehyde-ammonias presumably form as intermediate products. The carbonyl compounds mentioned, especially the aldehydes mentioned, are accessible, for example, by oxidation of the corresponding primary alcohols of formula II or by hydrogenation of the corresponding acid chlorides in the presence of Pd/$BaSO_4$ catalysts.

The cyclization of isonitriles of formula IV with the aid of lithium 2,2,6,6-tetramethylpiperidide is suitably carried out at temperatures of −100° to 0° C., preferably of −80° to −70° C., in an inert solvent, for example, a glycol ether, e.g., diglyme. The starting materials of formula IV are, for example, obtainable in situ from o-tolylisonitrile (which in the benzene ring can be monosubstituted or trisubstituted by alkyl, O-alkyl, S-alkyl, OH, F, Cl, Br, $CF_3$ and/or CN) and a halide of formula VI

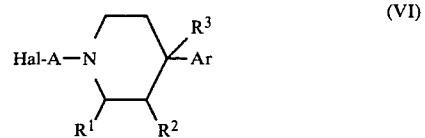

wherein Hal is Cl or Br and $R^1$, $R^2$, $R^3$, A and Ar are as defined above. (Compare J. Am. Chem. Soc. 99, (1977) 3532.)

Reduction of the pyridinium salts of formula V (in which An is preferably Cl or Br), for example with $NaBH_4$ in water, in alcohol, e.g., methanol or ethanol, or in mixtures of these solvents, if desired, with the addition of a base, e.g., NaOH, at temperatures of approximately 0° to 80° C. can result in the correspondin 3,4-dehydropiperidine derivatives (I, $R^2$ and $R^3$=a C—C bond).

Catalytic hydrogenation of V, on the other hand, as a rule, gives piperidine derivatives of formula I ($R^2=R^3=$H). Suitable catalysts for the catalytic hydrogenation are, for example, noble metal catalysts, nickel catalysts and cobalt catalysts. The noble metal catalysts can be on supports (for example, platinum of palladium on charcoal, or palladium on calcium carbonate or strontium carbonate), in the form of oxide catalysts (for example, platinum oxide) or in the form of finely divided metal catalysts. Nickel catalysts and cobalt catalysts are preferably employed in the form of Raney metals and nickel is also employed on kieselguhr or pumice as the support. The hydrogenation can be carried out at room temperature and normal pressure or at elevated temperatures and/or under elevated pressure. Preferably, the hydrogenation is carried out under pressures of from 1 to 100 atmospheres and at temperatures of −80° to +150° C., in particular from room temperature to +100° C. The reaction is preferably carried out in the acid, neutral or basic range and in the presence of a solvent, e.g., water, methanol, ethanol, isopropanol, n-butanol, ethyl acetate, dioxane, acetic acid or THF; mixtures of these solvents with one another can also be used.

Furthermore, in a compound of formula I one or two CO groups can optionally be reduced to $CH_2$ groups, for example, using diborane or using a complex metal hydride, e.g., $LiAlH_4$ in an ether, e.g., THF, and/or a double bond can be hydrogenated, for example, catalytically by one of the methods indicated above.

It is also possible to alkylate a resulting compound of formula I ($R^4=$H), in which case compounds of formula I ($R^4=$alkyl) are obtained.

Alkylating agents suitable for the alkylation are, for example, methyl chloride, methyl bromide, methyl iodide, methyl p-toluenesulphonate, dimethyl sulphate, ethyl chloride, ethyl bromide or ethyl iodide, n-propyl chloride, n-propyl bromide or n-propyl iodide, isopropyl chloride, isopropyl bromide or isopropyl iodide, n-butyl chloride, n-butyl bromide or n-butyl iodide or isobutyl chloride, isobutyl bromide or isobutyl iodide. Prior to the alkylation, the compounds of formula I are preferably converted to their metal derivatives, for example, by reaction with an alcoholate, e.g., sodium ethylate or potassium tert-butylate, a hydride, e.g., sodium hydride, an amide, e.g., sodium amide or lithium diisopropylamide, a metal-organic compound, e.g., n-butyl-Li or a metal, e.g., sodium (for example in liquid ammonia). This conversion is preferably carried out in an inert solvent, for example, an alcohol, e.g., methanol, ethanol or tert-butanol, an ether, e.g., diethyl ether, an amide, e.g., DMF, or a hydrocarbon, e.g., benzene, or also in mixtures of these solvents. The alkylation is preferably then carried out in the same reaction mixture. The reaction temperatures are as a rule from approximately −20° to +120° C., preferably approximately 0° to +80° C., and the reaction times are preferably approximately 1–48 hours.

Ethers of formula I wherein the benzene ring of the radical Ind is substituted 1 to 3 times by O-alkyl can be split according to methods which are known from the literature whereby the coresponding hydroxyindole derivatives are formed. One can split the ethers, for example, by treatment with HBr or HI in aqueous or acetic acid solution, by heating with Lewis acids such as AlCl$_3$ or boron trihalides or by fusion with pyridine- or aniline-hydrohalogenides, preferably pyridine-hydrochloride, at about 150° to 250° C.

A resulting base of formula I can be converted with an acid to the corresponding acid addition salt. Acids suitable for this reaction are those which give physiologically acceptable salts. Thus, it is possible to use inorganic acids, for example, sulphuric acid, hydrogen halide acids, e.g., hydrochloric acid or hydrobromic acid, phosphoric acids, e.g., orthophosphoric acid, nitric acid or sulphamic acid, and also organic acids, specifically aliphatic, alicyclic, araliphatic, aromatic or heterocyclic monobasic or polybasic carboxylic, sulphonic or sulphuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulphonic acid, ethanedisulphonic acid, 2-hydroxyethanesulphonic acid, benzenesulphonic acid, p-toluenesulphonic acid, naphthalene-mono- and -di-sulphonic acids and laurylsulphuric acid.

The free bases of formula I can, if desired, be liberated from their salts by treatment with strong bases, such as sodium hydroxide or potassium hydroxide, sodium carbonate or potassium carbonate.

It has been found that the compounds of formula I and their physiologically acceptable acid addition salts possess valuable pharmacological properties. Thus, in particular, they display effects on the central nervous system, above all dopaminestimulating effects and effects which inhibit the absorption of serotonin (anti-Parkinson and antidepressive effects). In detail, the compounds of the formula I induce contralateral turning movements in hemi-Parkinson rats (as can be demonstrated by the method of Ungerstedt et al, Brain Res. 24, (1970), 485–493) and lower the metabolism of dopamine in the brain (as can be demonstrated on rats by the method of Anden et al, Europ. J. Phamacol. 11, (1970), 303–314). In addition, the compounds inhibit the absorption of serotonin in synaptosomes in vitro (as can be demonstrated on rats by the method of Kannengiesser et al, Biochem. Pharmacol. 22, (1973), 73–84) and inhibit in vivo the liberation of serotonin in the brain induced by tyramine derivatives (as can be demonstrated on rats by the method of Carlsson et al, Europ. J. Pharmacol. 5, (1969), 357–366; 367–373). Furthermore, analgesic effects are found.

Compounds of formula I and their physiologically acceptable acid addition salts can therefore be used as medicinally active compounds and also as intermediate products for the preparation of other medicinally active compounds.

Thus, the invention also relates to the use of the compounds of formula I and of their physiologically acceptable salts for the preparation of pharmaceutical formulations, especially by a non-chemical route. The compounds can be brought into a suitable dosage form together with at least one excipient or auxiliary and optionally in combination with one or more additional active compounds.

The invention also relates to agents, especially pharmaceutical formulations, containing at least one compound of formula I and/or one of its physiologically acceptable acid addition salts. These formulations can be employed as medicaments in human medicine or veterinary medicine. Excipients which can be used are organic or inorganic substances which are suitable for enteral (for example, oral) or parenteral administration or topical application and do not react with the new compounds, for example, water, vegetable oils, benzyl alcohols, polyethylene glycols, gelatine, carbohydrates, e.g., lactose or starch, magnesium stearate, talc and petroleum jelly. Formulations used for enteral administration are, in particular, tablets, dragees, capsules, syrups, juices, drops or suppositories, formulations used for parenteral administration are solutions, preferably oily or aqueous solutions, and also suspensions, emulsions or implants and formulations used for topical application are ointments, creams or powders. The new compounds can also be lyophilized and the resulting lyophilizates can be used, for example, to prepare injection preparations. The indicated formulations can be sterilized and/or contain auxiliaries, e.g., as lubricants, preservatives, stabilizers and/or wetting agents, emulsifiers, salts for influencing the osmotic pressure, buffer substances, dyes, flavorings and/or aroma generating substances. If desired, they can also contain one or more additional active compounds, for example, one or more vitamins.

The invention also relates to the use of the compounds of formula I and of their physiologically acceptable acid addition salts in the therapeutic treatment of the human or animal body and in the control of diseases, especially Parkinsonism, extrapyramidal disorders arising during therapy with neuroleptic agents, depressions and side-effects arising during the treatment of hypertension (for example with α-methyldopa). Furthermore, the compounds can be used in endocrinology and gynaecology, for example, for the therapy of acromegalia, hypogonadism, secondary, amenorrhoea, the premenstrual syndrome, undesired puerperal lactation and generally as a prolactin inhibitor, and also for the therapy of cerebral disorders (for example, migraines), especially in geriatric medicine in the same way as certain ergot alkaloids.

The substances of this invention are as a rule administered analogously to known commercially available preparations (for example, bromocriptine and dihydroergocornine), preferably in dosages of approximately 0.2–500 mg and especially of 0.2–50 mg per dosage unit. The daily dose is preferably approximately 0.001–10 mg/kg of body weight. The low dosages (approximately 0.2 to 1 mg per dosage unit; approximately 0.001 to 0.005 mg/kg of body weight) are considered in particular for use as an agent against migraines; for the other indications dosages of 10–50 mg per dosage unit are preferred. The particular dose for each specific patient depends, of course, on the very diverse conventional factors, for example, on the effectiveness of the particular compound employed; on the age, the body weight, the general state of health and the sex of the patients; on the diet; on the time and mode of administration and on the rate of excretion; on the combination of medicaments used; and on the severity of the particular disease to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Each of the compounds of formula I named in the examples which follow is particularly suitable for the preparation of pharmaceutical formulations.

In the examples which follow, the term "customary working up" means:

Water is added, if necessary; the mixture is extracted with an organic solvent, e.g., benzene, chloroform or methylene chloride; the phases are separated; the organic phase is dried over sodium sulphate and filtered; the filtrate is evaporated and the residue is purified by chromatography and/or crystallization. Temperatures are given in degrees centigrade.

EXAMPLE 1

(a) A solution of 2.08 g of 3-(4-chlorobutyl)-indole (or 2.52 g of 3-(4-bromobutyl)-indole) and 1.6 g of 4-phenyl-3,4-dehydro-piperidine in 10 ml of acetonitrile is stirred at 20° for 12 hours and worked up in the customary manner and 3-[4-(4-phenyl-3,4-dehydro-1-piperidyl)-butyl]-indole hydrochloride is obtained; m.p. 206°–208°.

(b) 3.3 g of 3-]4-(4-phenyl-3,4-dehydro-1-piperidyl-butyl]-indole are dissolved in 25 ml of DMF; 0.24 g of NaH are added, while stirring and cooling; the mixture is stirred for a further 30 minutes; and a solution of 2 g of methyl iodide in 10 ml of DMF are added. The mixture is stirred at 25° for 16 hours. After customary working up, 1-methyl-3-[4-(4-phenyl-3,4-dehydro-1-piperidyl)-butyl]-indole is obtained; Rf 0.65 (toluene-/ethyl acetate, 95:5, on silica gel).

EXAMPLES 2 to 58

The following compounds are obtained analogously to Example 1 from the corresponding 3-(chloroalkyl)- or 3-(bromoalkyl)-indoles and the corresponding piperidine derivatives:

2. 1-Methyl-3-[4-(4-phenyl-3,4-dehydro-1-piperidyl)-butyl]-indole, RF 0.65 (toluene/ethyl acetate, 95:5).
3. 1-Ethyl-3-[4-(4-phenyl-3,4-dehydro-1-piperidyl)-butyl]-indole.
4. 1-n-Butyl-3-[4-(4-phenyl-3,4-dehydro-1-piperidyl)-butyl]-indole.
5. 1-Phenyl-3-[4-(4-phenyl-3,4-dehydro-1-piperidyl)-butyl]-indole, hydrochloride, m.p. 221°.
6. 2-Methyl-3-[4-(4-phenyl-3,4-dehydro-1-piperidyl)-butyl]-indole, hydrochloride, m.p. 216°–218°.
7. 2-Ethyl-3-[4-(4-phenyl-3,4-dehydro-1-piperidyl)-butyl]-indole.
8. 2-n-Butyl-3-[4-(4-phenyl-3,4-dehydro-1-piperidyl)-butyl]-indole.
9. 2-Phenyl-3-[4-(4-phenyl-3,4-dehydro-1-piperidyl)-butyl]-indole, hydrochloride, m.p. 193°–195°.
10. 1,2-Dimethyl-3-[4-(4-phenyl-3,4-dehydro-1-piperidyl)butyl]-indole.
11. 3-[4-(4-Phenyl-3,4-dehydro-1-piperidyl)-butyl]-5-methyl-indole.
12. 3-[4-(4-Phenyl-3,4-dehydro-1-piperidyl)-butyl]-5-ethyl-indole, m.p. 152°–154°.
13. 3-[4-(4-Phenyl-3,4-dehydro-1-piperidyl)-butyl]-5-methoxy-indole, hydrochloride, m.p. 181°.
14. 3-[4-(4-Phenyl-3,4-dehydro-1-piperidyl)-butyl]-5-fluoro-indole, hydrochloride, m.p. 229°.
15. 3-[4-(4-Phenyl-3,4-dehydro-1-piperidyl)-butyl]-5-chloro-indole, hydrochloride, m.p. 226°–228°.
16. 3-[4-(4-Phenyl-3,4-dehydro-1-piperidyl)-butyl]-5-bromo-indole.
17. 3-[4-(4-Phenyl-3,4-dehydro-1-piperidyl)-butyl]-5-trifluoromethyl-indole.
18. 3-[4-(4-Phenyl-3,4-dehydro-1-piperidyl)-butyl]-5-cyanoindole.
19. 3-[4-(4-Phenyl-3,4-dehydro-1-piperidyl)-butyl]-6-methoxy-indole, hydrochloride, m.p. 188°.
20. 3-[4-(4-Phenyl-3,4-dehydro-1-piperidyl)-butyl]-7-methyl-indole, hydrochloride, m.p. 206°–208°.
21. 3-[4-(4-Phenyl-3,4-dehydro-1-piperidyl)-butyl]-7-methyl-thio-indole.
22. 3-[4-(4-Phenyl-3,4-dehydro-1-piperidyl)-butyl]-7-trifluoromethyl-indole, m.p. 148°–150°.
23. 2,5-Dimethyl-3-[4-(4-phenyl-3,4-dehydro-1-piperidyl)-butyl]-indole.
24. 2-Methyl-3-[4-(4-phenyl-3,4-dehydro-1-piperidyl)-butyl]-5-methoxy-indole, m.p. 142°–144°.
25. 2-Methyl-3-[4-(4-phenyl-3,4-dehydro-1-piperidyl)-butyl]-5-chloro-indole, hydrochloride, m.p. 222°–224°.
26. 3-[4-(4-Phenyl-3,4-dehydro-1-piperidyl)-butyl]-4,7-dimethyl-indole.
27. 3-[4-(4-Phenyl-3,4-dehydro-1-piperidyl)-butyl]-4,5,6-trimethoxy-indole.
28. 3-[4-(4-Phenyl-3,4-dehydro-1-piperidyl)-butyl]-4-trifluoromethyl-7-chloro-indole.
29. 3-[4-(4-Phenyl-3,4-dehydro-1-piperidyl)-butyl]-5-methyl-7-chloro-indole.
30. 3-[4-(4-Phenyl-3,4-dehydro-1-piperidyl)-butyl]-5,6-dimethoxy-indole.
31. 3-[4-(4-Phenyl-3,4-dehydro-1-piperidyl)-butyl]-5,7-dimethoxy-indole.
32. 3-[4-(4-Phenyl-3,4-dehydro-1-piperidyl)-butyl]-5-fluoro-7-methyl-indole.
33. 3-[4-(4-Phenyl-3,4-dehydro-1-piperidyl)-butyl]-5,7-dichloro-indole.
34. 3-[4-(4-Phenyl-3,4-dehydro-1-piperidyl)-butyl]-5-chloro-7-methyl-indole.
35. 3-[4-(4-Phenyl-3,4-dehydro-1-piperidyl)-butyl]-5,6,7-trichloro-indole.
36. 3-[4-(2-Methyl-4-phenyl-3,4-dehydro-1-piperidyl)-butyl]-indole, hydrochloride, m.p. 218°–220°.
37. 3-[4-(4-Phenyl-1-piperidyl)-butyl]-indole, hydrochloride, m.p. 213°–215°.
38. 1-Methyl-3-[4-(4-phenyl-1-piperidyl)-butyl]-indole.
39. 1-Phenyl-3-[4-(4-phenyl-1-piperidyl)-butyl]-indole.
40. 2-Methyl-3-[4-(4-phenyl-1-piperidyl)-butyl]-indole.

41. 3-[4-(4-p-Tolyl-3,4-dehydro-1-piperidyl)-butyl]-indole.
42. 3-[4-(4-p-Fluorophenyl-3,4-dehydro-1-piperidyl)-butyl]-indole.
43. 3-[4-(4-o-Chlorophenyl-3,4-dehydro-1-piperidyl)-butyl]-indole.
44. 3-[4-(4-m-Chlorophenyl-3,4-dehydro-1-piperidyl)-butyl]-indole, hydrochloride, m.p. 260°-262°.
45. 3-[4-(4-p-Chlorophenyl-3,4-dehydro-1-piperidyl)-butyl]-indole.
46. 3-[4-(4-p-Bromophenyl-3,4-dehydro-1-piperidyl)-butyl]-indole.
47. 3-[4-(4-p-Iodophenyl-3,4-dehydro-1-piperidyl)-butyl]-indole.
48. 3-[4-(4-m-Trifluoromethylphenyl-3,4-dehydro-1-piperidyl]-butyl]-indole.
49. 1-Methyl-3-[4-(4-p-chlorophenyl-3,4-dehydro-1-piperidyl)-butyl]-indole.
50. 2-Methyl-3-[4-(4-p-chlorophenyl-3,4-dehydro-1-piperidyl)-butyl]-indole, hydrochloride, m.p. 243°-245°.
51. 3-[4-(4-p-Tolyl-1-piperidyl)-butyl]-indole.
52. 3-[4-(4-p-Fluorophenyl-1-piperidyl)-butyl]-indole.
53. 3-[4-(4-o-Chlorophenyl-1-piperidyl)-butyl]-indole.
54. 3-[4-(4-m-Chlorophenyl-1-piperidyl)-butyl]-indole.
55. 3-[4-(4-p-Chlorophenyl-1-piperidyl)-butyl]-indole.
56. 3-[4-(4-p-Bromophenyl-1-piperidyl)-butyl]-indole.
57. 3-[4-(4-p-Iodophenyl-1-piperidyl)-butyl]-indole.
58. 3-[4-(4-m-Trifluoromethylphenyl-1-piperidyl)-butyl]-indole.

EXAMPLE 59

A mixture of 4.43 g of 3-(4-p-toluenesulphonyloxybutyl)-indole and 3.18 g of 4-phenyl-3,4-dehydro-piperidine is heated to 130°. After the exothermic reaction has subsided and after cooling, the reaction mixture is worked up in the customary manner and 3-[4-(4-phenyl-3,4-dehydro-1-piperidyl)-butyl]-indole is obtained; hydrochloride, m.p. 206°-208°.

EXAMPLE 60

2.99 g of 3-(4-iodobutyl)-indole, 1.59 g of 4-phenyl-3,4-dehydro-piperidine and 1.5 g of anhydrous potassium carbonate are boiled in 25 ml of n-butanol for 2 hours, while stirring; the mixture is allowed to cool and is worked up in the customary manner and 3-[4-(4-phenyl-3,4-dehydro-1-piperidyl)-butyl]indole is obtained. Hydrochloride, m.p. 206°-208°.

EXAMPLE 61

(a) 1.62 g of carbonyldiimidazole are added to a solution of 2.03 g of 4-(3-indolyl)-butyric acid in 10 ml of THF; the mixture is stirred at 20 for one hour; and a solution of 1.59 g of 4-phenyl-3,4-dehydropiperidine in 50 ml of THF is then added. The mixture is stirred at 20° for 1.5 hours and worked up in the customary manner and 3-[4-oxo-4-(4-phenyl-3,4-dehydro-1-piperidyl)-butyl]-indole is obtained; m.p. 129°-131°.

(b) A solution of 3.44 g of 3-[4-oxo-4-(4-phenyl-3,4-dehydro-1-piperidyl)-butyl]-indole in 10 ml of THF is added dropwise to a suspension of 0.38 g of LiAlH$_4$ in 10 ml of THF, while stirring. After the reaction has subsided, 5 ml of ethyl acetate are added and the mixture is worked up in the customary manner and 3-[4-(4-phenyl-3,4-dehydro-1-piperidyl)-butyl]-indole is obtained; hydrochloride, m.p. 206°-208°.

EXAMPLES 62-170

The following compounds are obtained analogously to Example 61a) from the corresponding 3-indolylalkanoic acids and the corresponding amines:

62. 1-Methyl-3-[4-oxo-4-(4-phenyl-3,4-dehydro-1-piperidyl)-butyl]-indole.
63. 1-Ethyl-3-[4-oxo-4-(4-phenyl-3,4-dehydro-1-piperidyl)-butyl]-indole.
64. 1-n-Butyl-3-[4-oxo-4-(4-phenyl-3,4-dehydro-1-piperidyl)-butyl]-indole.
65. 2-Methyl-3-[4-oxo-4-(4-phenyl-3,4-dehydro-1-piperidyl)-butyl]-indole.
66. 2-Ethyl-3-[4-oxo-4-(4-phenyl-3,4-dehydro-1-piperidyl)-butyl]-indole.
67. 2-n-Butyl-3-[4-oxo-4-(4-phenyl-3,4-dehydro-1-piperidyl)-butyl]-indole.
68. 2-Phenyl-3-[4-oxo-4-(4-phenyl-3,4-dehydro-1-piperidyl)-butyl]-indole.
69. 1,2-Dimethyl-3-[4-oxo-4-(4-phenyl-3,4-dehydro-1-piperidyl)-butyl]-indole.
70. 3-[4-Oxo-4-(4-phenyl-3,4-dehydro-1-piperidyl)-butyl]-5-methyl-indole.
71. 3-[4-Oxo-4-(4-phenyl-3,4-dehydro-1-piperidyl)-butyl]-5-ethyl-indole.
72. 3-[4-Oxo-4-(4-phenyl-3,4-dehydro-1-piperidyl)-butyl]-5-methoxy-indole.
73. 3-[4-Oxo-4-(4-phenyl-3,4-dehydro-1-piperidyl)-butyl]-5-fluoro-indole, m.p. 131°.
74. 3-[4-Oxo-4-(4-phenyl-3,4-dehydro-1-piperidyl)-butyl]-5-chloro-indole.
75. 3-[4-Oxo-4-(4-phenyl-3,4-dehydro-1-piperidyl)-butyl]-5-bromo-indole.
76. 3-[4-Oxo-4-(4-phenyl-3,4-dehydro-1-piperidyl)-butyl]-5-trifluoromethyl-indole.
77. 3-[4-Oxo-4-(4-phenyl-3,4-dehydro-1-piperidyl)-butyl]-5-cyano-indole.
78. 3-[4-Oxo-4-(4-phenyl-3,4-dehydro-1-piperidyl)-butyl]-6-methoxy-indole.
79. 3-[4-Oxo-4-(4-phenyl-3,4-dehydro-1-piperidyl)-butyl]-7-methyl-indole.
80. 3-[4-Oxo-4-(4-phenyl-3,4-dehydro-1-piperidyl)-butyl]-7-methylthio-indole.
81. 3-[4-Oxo-4-(4-phenyl-3,4-dehydro-1-piperidyl)-butyl]-7-trifluoromethyl-indole.
82. 2,5-Dimethyl-3-[4-oxo-4-(4-phenyl-3,4-dehydro-1-piperidyl)-butyl]-indole.
83. 2-Methyl-3-[4-oxo-4-(4-phenyl-3,4-dehydro-1-piperidyl)-butyl]-5-methoxy-indole.
84. 2-Methyl-3-[4-oxo-4-(4-phenyl-3,4-dehydro-1-piperidyl)-butyl]-5-chloro-indole.
85. 3-[4-Oxo-4-(4-phenyl-3,4-dehydro-1-piperidyl)-butyl]-4,7-dimethyl-indole.
86. 3-[4-Oxo-4-(4-phenyl-3,4-dehydro-1-piperidyl)-butyl]-4,5,6-trimethoxy-indole.
87. 3-[4-Oxo-4-(4-phenyl-3,4-dehydro-1-piperidyl)-butyl]-4-trifluoromethyl-7-chloro-indole.
88. 3-[4-Oxo-4-(4-phenyl-3,4-dehydro-1-piperidyl)-butyl]-5-methyl-7-chloro-indole.
89. 3-[4-Oxo-4-(4-phenyl-3,4-dehydro-1-piperidyl)-butyl]-5,6-dimethoxy-indole.
90. 3-[4-Oxo-4-(4-phenyl-3,4-dehydro-1-piperidyl)-butyl]-5,7-dimethoxy-indole.
91. 3-[4-Oxo-4-(4-phenyl-3,4-dehydro-1-piperidyl)-butyl]-5-fluoro-7-methyl-indole.
92. 3-[4-Oxo-4-(4-phenyl-3,4-dehydro-1-piperidyl)-butyl]-5,7-dichloro-indole.

93. 3-[4-Oxo-4-(4-phenyl-3,4-dehydro-1-piperidyl)-butyl]-5-chloro-7-methyl-indole.
94. 3-[4-Oxo-4-(4-phenyl-3,4-dehydro-1-piperidyl)-butyl]-5,6,7-trichloro-indole.
95. 3-[4-Oxo-4-(2-methyl-4-phenyl-3,4-dehydro-1-piperidyl)-butyl]-indole.
96. 3-[4-Oxo-4-(4-phenyl-1-piperidyl)-butyl]-indole.
97. 1-Methyl-3-[4-oxo-4-(4-phenyl-1-piperidyl)-butyl]-indole.
98. 3-[4-Oxo-4-(4-p-tolyl-3,4-dehydro-1-piperidyl)-butyl]-indole.
99. 3-[4-Oxo-4-(4-p-fluorophenyl-3,4-dehydro-1-piperidyl)-butyl]-indole.
100. 3-[4-Oxo-4-(4-o-chlorophenyl-3,4-dehydro-1-piperidyl)-butyl]-indole.
101. 3-[4-Oxo-4-(4-m-chlorophenyl-3,4-dehydro-1-piperidyl)-butyl]-indole.
102. 3-[4-Oxo-4-(4-p-chlorophenyl-3,4-dehydro-1-piperidyl)-butyl]-indole.
103. 3-[4-Oxo-4-(4-p-bromophenyl-3,4-dehydro-1-piperidyl)-butyl]-indole.
104. 3-[4-Oxo-4-(4-p-iodophenyl-3,4-dehydro-1-piperidyl)-butyl]-indole.
105. 3-[4-Oxo-4-(4-m-trifluoromethylphenyl-3,4-dehydro-1-piperidyl)-butyl]-indole.
106. 1-Methyl-3-[4-oxo-4-(4-p-chlorophenyl-3,4-dehydro-1-piperidyl)-butyl]-indole.
107. 2-Methyl-3-[4-oxo-4-(4-p-chlorophenyl-3,4-dehydro-1-piperidyl)-butyl]-indole.
108. 3-[4-Oxo-4-(4-p-tolyl-1-piperidyl)-butyl]-indole.
109. 3-[4-Oxo-4-(4-p-fluorophenyl-1-piperidyl)-butyl]-indole.
110. 3-[4-Oxo-4-(4-o-chlorophenyl-1-piperidyl)-butyl]-indole.
111. 3-[4-Oxo-4-(4-m-chlorophenyl-1-piperidyl)-butyl]-indole.
112. 3-[4-Oxo-4-(4-p-chlorophenyl-1-piperidyl)-butyl]-indole.
113. 3-[4-Oxo-4-(4-p-bromophenyl-1-piperidyl)-butyl]-indole.
114. 3-[4-Oxo-4-(4-p-iodophenyl-1-piperidyl)-butyl]-indole.
115. 3-[4-Oxo-4-(4-m-trifluoromethylphenyl-1-piperidyl)-butyl]-indole.
116. 3-[1,4-Dioxo-4-(4-phenyl-3,4-dehydro-1-piperidyl)-butyl]-indole.
117. 1-Methyl-3-[1,4-dioxo-4-(4-phenyl-3,4-dehydro-1-piperidyl)-butyl]-indole.
118. 1-Ethyl-3-[1,4-dioxo-4-(4-phenyl-3,4-dehydro-1-piperidyl)-butyl]-indole.
119. 1-n-Butyl-3-[1,4-dioxo-4-(4-phenyl-3,4-dehydro-1-piperidyl)-butyl]-indole.
120. 2-Methyl-3-[1,4-dioxo-4-(4-phenyl-3,4-dehydro-1-piperidyl)-butyl]-indole.
121. 2-Ethyl-3-[1,4-dioxo-4-(4-phenyl-3,4-dehydro-1-piperidyl)-butyl]-indole.
122. 2-n-Butyl-3-[1,4-dioxo-4-(4-phenyl-3,4-dehydro-1-piperidyl)-butyl]-indole.
123. 2-Phenyl-3-[1,4-dioxo-4-(4-phenyl-3,4-dehydro-1-piperidyl)-butyl]-indole, m.p. 152°–154°.
124. 1,2-Dimethyl-3-[1,4-dioxo-4-(4-phenyl-3,4-dehydro-1-piperidyl)-butyl]-indole.
125. 3-[1,4-Dioxo-4-(4-phenyl-3,4-dehydro-1-piperidyl)-butyl]-5-methyl-indole.
126. 3-[1,4-Dioxo-4-(4-phenyl-3,4-dehydro-1-piperidyl)-butyl]-5-ethyl-indole.
127. 3-[1,4-Dioxo-4-(4-phenyl-3,4-dehydro-1-piperidyl)-butyl]-5-methoxy-indole.
128. 3-[1,4-Dioxo-4-(4-phenyl-3,4-dehydro-1-piperidyl)-butyl]-5-fluoro-indole.
129. 3-[1,4-Dioxo-4-(4-phenyl-3,4-dehydro-1-piperidyl)-butyl]-5-chloro-indole, m.p. 200°–202°.
130. 3-[1,4-Dioxo-4-(4-phenyl-3,4-dehydro-1-piperidyl)-butyl]-5-bromo-indole.
131. 3-[1,4-Dioxo-4-(4-phenyl-3,4-dehydro-1-piperidyl)-butyl]-5-trifluoromethyl-indole.
132. 3-[1,4-Dioxo-4-(4-phenyl-3,4-dehydro-1-piperidyl)-butyl]-5-cyano-indole, m.p. 220°–222°.
133. 3-[1,4-Dioxo-4-(4-phenyl-3,4-dehydro-1-piperidyl)-butyl]-6-methoxy-indole.
134. 3-[1,4-Dioxo-4-(4-phenyl-3,4-dehydro-1-piperidyl)-butyl]-7-methyl-indole.
135. 3-[1,4-Dioxo-4-(4-phenyl-3,4-dehydro-1-piperidyl)-butyl]-7-methylthio-indole.
136. 3-[1,4-Dioxo-4-(4-phenyl-3,4-dehydro-1-piperidyl)-butyl]-7-trifluoromethyl-indole.
137. 2,5-Dimethyl-3-[1,4-dioxo-4-(4-phenyl-3,4-dehydro-1-piperidyl)-butyl]-indole, m.p. 201°–203°.
138. 2-Methyl-3-[1,4-dioxo-4-(4-phenyl-3,4-dehydro-1-piperidyl)-butyl]-5-methoxy-indole, m.p. 185°–187°.
139. 2-Methyl-3-[1,4-dioxo-4-(4-phenyl-3,4-dehydro-1-piperidyl)-butyl]-5-chloro-indole.
140. 3-[1,4-Dioxo-4-(4-phenyl-3,4-dehydro-1-piperidyl)-butyl]-4,7-dimethyl-indole.
141. 3-[1,4-Dioxo-4-(4-phenyl-3,4-dehydro-1-piperidyl)-butyl]-4,5,6-trimethoxy-indole.
142. 3-[1,4-Dioxo-4-(4-phenyl-3,4-dehydro-1-piperidyl)-butyl]-4-trifluoromethyl-7-chloro-indole.
143. 3-[1,4-Dioxo-4-(4-phenyl-3,4-dehydro-1-piperidyl)-butyl]-5-methyl-7-chloro-indole.
144. 3-[1,4-Dioxo-4-(4-phenyl-3,4-dehydro-1-piperidyl)-butyl]-5,6-dimethoxy-indole.
145. 3-[1,4-Dioxo-4-(4-phenyl-3,4-dehydro-1-piperidyl)-butyl]-5,7-dimethoxy-indole.
146. 3-[1,4-Dioxo-4-(4-phenyl-3,4-dehydro-1-piperidyl)-butyl]-5-fluoro-7-methyl-indole.
147. 3-[1,4-Dioxo-4-(4-phenyl-3,4-dehydro-1-piperidyl)-butyl]-5,7-dichloro-indole.
148. 3-[1,4-Dioxo-4-(4-phenyl-3,4-dehydro-1-piperidyl)-butyl]-5-chloro-7-methyl-indole.
149. 3-[1,4-Dioxo-4-(4-phenyl-3,4-dehydro-1-piperidyl)-butyl]-5,6,7-trichloro-indole.
150. 3-[1,4-Dioxo-4-(2-methyl-4-phenyl-3,4-dehydro-1-piperidyl)-butyl]-indole.
151. 3-[1,4-Dioxo-4-(4-phenyl-1-piperidyl)-butyl]-indole.
152. 1-Methyl-3-[1,4-dioxo-4-(4-phenyl-1-piperidyl)-butyl]-indole.
153. 3-[1,4-Dioxo-4-(4-p-tolyl-3,4-dehydro-1-piperidyl)-butyl]-indole.
154. 3-[1,4-Dioxo-4-(4-p-fluorophenyl-3,4-dehydro-1-piperidyl)-butyl]-indole.
155. 3-[1,4-Dioxo-4-(4-o-chlorophenyl-3,4-dehydro-1-piperidyl)-butyl]-indole.
156. 3-[1,4-Dioxo-4-(4-m-chlorophenyl-3,4-dehydro-1-piperidyl)-butyl]-indole.
157. 3-[1,4-Dioxo-4-(4-p-chlorophenyl-3,4-dehydro-1-piperidyl)-butyl]-indole.
158. 3-[1,4-Dioxo-4-(4-p-bromophenyl-3,4-dehydro-1-piperidyl)-butyl]-indole.
159. 3-[1,4-Dioxo-4-(4-p-iodophenyl-3,4-dehydro-1piperidyl)-butyl]-indole.
160. 3-[1,4-Dioxo-4-(4-m-trifluoromethylphenyl-3,4-dehydro-1-piperidyl)-butyl]-indole.
161. 1-Methyl-3-[1,4-dioxo-4-(4-p-chlorophenyl-3,4-dehydro-1-piperidyl)-butyl]-indole.

162. 2-Methyl-3-[1,4-dioxo-4-(4-p-chlorophenyl-3,4-dehydro-1-piperidyl)-butyl]-indole, m.p. 227°-229°.
163. 3-[1,4-Dioxo-4-(4-p-tolyl-1-piperidyl)-butyl]-indole.
164. 3-[1,4-Dioxo-4-(4-p-fluorophenyl-1-piperidyl)-butyl]-indole.
165. 3-[1,4-Dioxo-4-(4-o-chlorophenyl-o-piperidyl)-butyl]-indole.
166. 3-[1,4-Dioxo-4-(4-m-chlorophenyl-1-piperidyl)-butyl]-indole.
167. 3-[1,4-Dioxo-4-(4-p-chlorophenyl-1-piperidyl)-butyl]-indole.
168. 3-[1,4-Dioxo-4-(4-p-bromophenyl-1-piperidyl)-butyl]-indole.
169. 3-[1,4-Dioxo-4-(4-p-iodophenyl-1-piperidyl)-butyl]-indole.
170. 3-[1,4-Dioxo-4-(4-m-trifluoromethylphenyl-1-piperidyl)butyl]-indole.

EXAMPLE 171

A mixture of 1.88 g of 3-(4-aminobutyl)-indole [obtainable by reacting 3-(4-bromobutyl)-indole with phthalimide potassium and subsequently hydrolyzing the reaction product] and 2.15 g of 1,5-dichloro-3-phenyl-2-pentene (obtainable by reducing diethyl 3-phenyl-2-pentene-1,5-dicarboxylate with LiAlH$_4$ and subsequently reacting the product with SOCl$_2$) in 40 ml of acetone and 40 ml of water is boiled for 24 hours and worked up in the customary manner. 3-[4-(4-Phenyl-3,4-dehydro-1-piperidyl)-butyl]-indole is obtained; hydrochloride, m.p. 206√-208°.

EXAMPLE 172

A solution of 2.14 g of lithium diisopropylamide in 10 ml of diglyme is added dropwise at −78° to a solution of 1.17 g of o-tolylisonitrile in 10 ml of diglyme. 5.88 g of 4-(4-phenyl-3,4-dehydro-1-piperidyl)-butyl bromide are added to the resulting solution at −78°. After customary working up, o-[4-(4-phenyl-3,4-dehydro-1-piperidyl)-butyl]-phenyl-isonitrile is obtained; this is taken up as the crude product in 10 ml of diglyme and a solution of 2.94 g of lithium 2,2,6,6-tetramethyl-piperidide is added at −78°. The temperature is allowed to rise to 20°; the reaction mixture is worked up in the customary manner; and 3-[4-(4-phenyl-3,4-dehydro-1-piperidyl)-butyl]-indole is obtained; hydrochloride, m.p. 206°-208°.

EXAMPLE 173

(a) 1 g of NaBH$_4$ in 20 ml of water is added to a solution of 4.07 g of 1-[4-(3-indolyl)-butyl]-4-phenyl-pyridinium bromide [obtainable from 3-(4-bromobutyl)-indole and 4-phenyl-pyridine] in 50 ml of 1 N NaOH, while stirring; and the mixture is then stirred for a further 3 hours at 60°. After customary working up, 3-[4-(4-phenyl-3,4-dehydro-1-piperidyl)-butyl]-indole is obtained; hydrochloride, m.p 206°-208°.

(b) 1 g of 3-[4-(4-phenyl-3,4-dehydro-1-piperidyl)-butyl]-indole is dissolved in 25 ml of dioxane and hydrogenated on 0.2 g of 5% Pd-on-charcoal at 40° and normal pressure until the reaction has ceased; the reaction mixture is filtered; the filtrate is evaporated; and, after customary working up, 3-[4-(4-phenyl-1-piperidyl)-butyl]-indole is obtained; hydrochloride, m.p. 213°-215°.

EXAMPLE 174

1 g of 1-[4-(3-indolyl)-butyl]-4-phenylpyridinium chloride is dissolved in 25 ml of methanol and hydrogenated on 0.1 g of platinum at 25° and normal pressure until the reaction has ceased; the reaction mixture is filtered; the filtrate is evaporated; and, after customary working up, 3-[4-(4-phenyl-1-piperidyl)-butyl]-indole is obtained; hydrochloride, m.p. 213°-215°.

EXAMPLE 175

A mixture of 3.97 g of 3-[4-(4-phenyl-3,4-dehydro-1-piperidyl)-butyl]-5-methoxy-indole hydrochloride and 3.5 g of pyridine hydrochloride is stirred for 3 hours at 160°. After customary working up, one obtains 3-[4-(4-phenyl-3,4-dehydro-1-piperidyl)-butyl]-5-hydroxy-indole; hydrochloride, m.p. 258°.

EXAMPLE 176

Analogously to Example 175, one obtains 3-[4-(4-phenyl-3,4-dehydro-1-piperidyl)-butyl]-6-hydroxy-indole from the corresponding 6-methoxy compound. Hydrochloride, m.p. 271°.

The examples which follow relate to pharmaceutical formulations which contain amines of formula I or their acid addition salts:

EXAMPLE A: TABLETS

A mixture of 1 kg of 3-[4-(4-phenyl-3,4-dehydro-1-piperidyl)-butyl]-indole hydrochloride, 4 kg of lactose, 1.2 kg of potato starch, 0.2 kg of talc and 0.1 kg of magnesium stearate is compressed into tablets in the customary manner, so that each tablet contains 10 mg of the active compound.

EXAMPLE B: DRAGEES

Tablets are compressed analogously to EXAMPLE A and these are subsequently coated in the customary manner with a coating of sucrose, potato starch, talc, tragacanth and a dyestuff.

EXAMPLE C: CAPSULES 2 kg of 3-[4-(4-phenyl-3,4-dehydro-1-piperidyl)-butyl]-indole hydrochloride are filled into hard gelatine capsules in the customary manner, so that each capsule contains 20 mg of the active compound.

EXAMPLE D: AMPOULES

A solution of 1 kg of 3-[4-(4-phenyl-3,4-dehydro-1-piperidyl)-butyl]-indole hydrochloride in 30 liters of twice distilled water is sterile-filtered, filled into ampoules and lyophilized under sterile conditions and the ampoules are sealed under sterile conditions. Each ampoule contains 10 mg of the active compound. Tablets, dragees, capsules and ampoules which contain one or more of the other active compounds of formula I and/or their physiologically acceptable acid addition salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An indolealkylamine of the formula

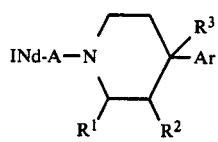

wherein Ind is 1-R⁴-2-R⁵-indol-3-yl or the corresponding group in which the benzene ring is monosubstituted to trisubstituted by alkyl, O-alkyl, S-alkyl, OH, F, Cl, Br, $CF_3$ or CN; A is $-(CH_2)_4-$, $-(CH_2)_3-CO-$ or $-CO-(CH_2)_2-CO-$; $R^1$ is H or methyl; $R^2$ is H or together with $R^3$ is a C—C bond; $R^3$ is H or together with $R^2$ is a C—C bond; $R^4$ and $R^5$ are each H, alkyl or phenyl; and Ar is phenyl or phenyl monosubstituted or disubstituted by alkyl, F, Cl, Br, I or $CF_3$; wherein alkyl in each case is of 1-4 carbon atoms; and the physiologically acceptable acid addition salts thereof.

2. A compound of claim 1, wherein Ind is indol-3-yl, 1-methyl-indol-3-yl or 2-methyl-indol-3-yl.

3. A compound of claim 1, wherein A is $-(CH_2)_4-$.

4. A compound of claim 1, wherein $R^1$ is H.

5. A compound of claim 1, wherein $R^2$ and $R^3$ together are a C—C bond.

6. A compound of claim 1, wherein Ar is phenyl, p-fluorophenyl, o- or p-chlorophenyl, o- or p-bromophenyl, p-tolyl or m-trifluoromethylphenyl.

7. A compound of claim 2, wherein A is $-(CH_2)_4-$ and Ar is phenyl, p-chlorophenyl or m-trifluoromethylphenyl.

8. A compound of claim 7, wherein Ar is phenyl.

9. 3-[4-(4-Phenyl-3,4-dehydro-1-piperidyl)-butyl]-indole, a compound of claim 1.

10. A pharmaceutical composition comprising an amount of a compound of claim 1 effective to treat Parkinsonism and a pharmaceutically acceptable adjuvant.

11. The composition of claim 10, wherein the amount of a compound of claim 1 is 0.2–500 mg.

12. A method of treating Parkinsonism which comprises administering an amount of a compound of claim 1 effective for said treatment.

* * * * *